(12) United States Patent
Belack et al.

(10) Patent No.: US 9,126,186 B2
(45) Date of Patent: Sep. 8, 2015

(54) PROCESS FOR PRODUCING THERMALLY SURFACE POSTCROSSLINKED WATER-ABSORBING POLYMER PARTICLES

(71) Applicant: BASF SE, Ludwigshafen (DE)

(72) Inventors: Joerg Belack, Damschied (DE); Thomas Daniel, Waldsee (DE); Christophe Bauduin, Plankstadt (DE)

(73) Assignee: BASF SE, Ludwigshafen (DE)

( * ) Notice: Subject to any disclaimer, the term of this patent is extended or adjusted under 35 U.S.C. 154(b) by 226 days.

(21) Appl. No.: 13/672,129

(22) Filed: Nov. 8, 2012

(65) Prior Publication Data

US 2013/0310250 A1 Nov. 21, 2013

Related U.S. Application Data

(60) Provisional application No. 61/561,293, filed on Nov. 18, 2011.

(30) Foreign Application Priority Data

Nov. 18, 2011 (EP) .................................... 11189744

(51) Int. Cl.
*B01J 20/26* (2006.01)
*A61L 15/60* (2006.01)
*C08J 3/24* (2006.01)
*A61L 15/24* (2006.01)

(52) U.S. Cl.
CPC ................ *B01J 20/267* (2013.01); *A61L 15/24* (2013.01); *A61L 15/60* (2013.01); *C08J 3/245* (2013.01); *C08J 2333/02* (2013.01)

(58) Field of Classification Search
CPC ....... C08J 2333/02; C08J 3/245; A61L 15/60; A61L 15/24; B01J 20/267
USPC ......................................................... 502/402
See application file for complete search history.

(56) References Cited

U.S. PATENT DOCUMENTS

| 6,239,230 B1 | 5/2001 | Eckert et al. |
| 2005/0256757 A1 | 11/2005 | Sierra et al. |
| 2010/0247916 A1 | 9/2010 | Hamilton et al. |

FOREIGN PATENT DOCUMENTS

| WO | WO-2004/069915 A2 | 8/2004 |
| WO | WO-2006/025586 A1 | 3/2006 |
| WO | WO-2009/041731 A1 | 4/2009 |

OTHER PUBLICATIONS

International Search Report in international application No. PCT/EP2012/072493, dated Feb. 15, 2013 (translation).
Buchholz, Fredric L., et al. *Modern Superabsorbent Polymer Technology,* "Commercial Processes for the Manufacture of Superabsorbent Polymers." New York: John Wiley S. Sons, Inc., 1998, pp. 71-103.

*Primary Examiner* — Colleen Dunn
*Assistant Examiner* — Haytham Soliman
(74) *Attorney, Agent, or Firm* — Marshall, Gerstein & Borun LLP

(57) ABSTRACT

A process for producing thermally surface postcrosslinked water-absorbing polymer particles, wherein the water-absorbing polymer particles are coated before, during or after the thermal surface postcrosslinking with at least one complex consisting of a polyvalent metal salt and a 2-hydroxycarboxamide.

7 Claims, No Drawings

PROCESS FOR PRODUCING THERMALLY SURFACE POSTCROSSLINKED WATER-ABSORBING POLYMER PARTICLES

CROSS-REFERENCE TO RELATED APPLICATIONS

This application claims the benefit of European Patent Application No. 11189744.3, filed Nov. 18, 2011, and U.S. Provisional Patent Application No. 61/561,293, filed Nov. 18, 2011, incorporated herein by reference in its entirety.

The present invention relates to a process for producing thermally surface postcrosslinked water-absorbing polymer particles, wherein the water-absorbing polymer particles are coated before, during or after the thermal surface postcrosslinking with at least one complex consisting of a polyvalent metal salt and a 2-hydroxycarboxamide.

Water-absorbing polymers are especially polymers formed from (co)polymerized hydrophilic monomers, graft (co)polymers of one or more hydrophilic monomers on a suitable graft base, crosslinked cellulose ethers or starch ethers, crosslinked carboxymethylcellulose, partially crosslinked polyalkylene oxide, or natural products swellable in aqueous liquids, for example guar derivatives. Being products which absorb aqueous solutions, such polymers are used to produce diapers, tampons, sanitary napkins and other hygiene articles, but also as water-retaining agents in market gardening. The water-absorbing polymers are often also referred to as "absorbent resins", "superabsorbents", "superabsorbent polymers", "absorbent polymers", "absorbent gelling materials", "hydrophilic polymers" or "hydrogels".

The production of water-absorbing polymers is described in the monograph "Modern Superabsorbent Polymer Technology", F. L. Buchholz and A. T. Graham, Wiley-VCH, 1998, pages 71 to 103.

To improve the performance properties, for example liquid conductivity in the diaper and absorption capacity under pressure, water-absorbing polymer particles are generally surface postcrosslinked. This surface postcrosslinking can be performed in aqueous gel phase. Preferably, however, dried, ground and classified polymer particles (base polymer) are surface coated with a surface postcrosslinker and thermally surface postcrosslinked. Crosslinkers suitable for this purpose are compounds which comprise at least two groups which can form covalent bonds with the carboxylate groups of the water-absorbing polymer particles.

The saline liquid conductivity can be determined, for example, via the gel bed permeability (GBP) to US 2005/0256757.

WO 2004/069915 A2 describes a process for producing water-absorbing polymer particles with high saline flow conductivity (SFC), which simultaneously possess strong wicking action, which means that the aqueous liquids can absorb counter to gravity. The wicking action of the polymer particles is achieved by specific surface properties. For this purpose, particles with a size of less than 180 µm are sieved out of the base polymer, agglomerated and combined with the previously removed particles larger than 180 µm.

WO 2009/041731 A1 teaches improving saline flow conductivity (SFC) and centrifuge retention capacity (CRC) by coating with polyvalent metal cations and fatty acids. Fatty acids, however, also lower the surface tension of the aqueous extract of the water-absorbing polymer particles and hence increase the risk of leakage of the diaper.

US 2010/0247916 discloses the use of basic salts of polyvalent metal cations, especially for improvement of gel bed permeability (GBP) and absorbency under a pressure of 49.2 $g/cm^2$ (AUL0.7 psi).

For ultrathin hygiene articles, preferably water-absorbing polymer particles without any coarse grains (particles) are required, since these would be perceptible and can be rejected by consumers. However, it may be necessary for economic reasons to consider the entire diaper construction in the optimization of the particle size distribution of the water-absorbing polymer particles. A coarser particle size distribution can lead to a better ratio of absorption capacity and liquid conductivity in the diaper, but it is typically necessary for this purpose to place a suitable fibrous liquid distribution layer on the absorbent core, or to cover the rough powder with a soft nonwoven at the back too.

In ultrathin hygiene articles, this plays an important role since they can comprise absorbent cores which consist to an extent of 50 to 100% by weight of water-absorbing polymer particles, such that the polymer particles in use assume both the storage function for the liquid and the function of active (wicking action) and passive liquid transport (liquid conductivity). The more cellulose is replaced by water-absorbing polymer particles or synthetic fibers, the more transport functions have to be fulfilled by the water-absorbing polymer particles in addition to their storage function.

The present invention therefore provides suitable water-absorbing polymer particles for hygiene articles which comprise, in at least part of the absorbent core or in the entire absorbent core, a concentration of water-absorbing polymer particles of at least 50% by weight, preferably at least 60% by weight, more preferably at least 70% by weight, even more preferably at least 80% by weight, most preferably of 90 to 100% by weight. The absorbent core is the part of the hygiene article which serves for the storage and retention of the aqueous body fluid to be absorbed. It typically often consists of a mixture of fibers, for example cellulose, and the water-absorbing polymer particles distributed therein. Optionally, it is also possible to use binders and adhesives to hold the absorbent core together. Alternatively, the water-absorbing polymer particles can also be enclosed in pockets between at least two nonwovens bonded to one another. The other constituents of the hygiene article, including the optional envelope and cover of the absorbent core, are not considered to form part of the absorbent core in the context of this invention.

To produce such water-absorbing polymer particles, coatings of polyvalent cations are typically used. Particularly suitable salts of polyvalent metal cations are soluble salts such as aluminum sulfate, polyamines, and water-insoluble phosphates of polyvalent metal cations such as calcium, zirconium, iron and aluminum.

The salts of polyvalent metal cations, especially of aluminum, zirconium and iron, are suitable for achieving the desired effects on liquid conductivity, but the success depends on the anion present. When, for example, aluminum sulfate is used, lumps or dust are formed readily even in the course of coating of the water-absorbing polymer particles; moreover, absorption capacity under pressure is reduced. The use of aluminum lactate can likewise lead to dust problems and, moreover, the lactic acid present in free form in the course of coating of the water-absorbing polymer particles is highly corrosive. The lactic acid can also condense to polylactic acid in the course of concentration by removal of water after the coating, which can make the surface of the water-absorbing polymer particles coated therewith undesirably tacky. This can impair the flow properties of the water-absorbing polymer particles.

Other aluminum salts or salts of polyvalent cations with many organic anions either do not act in the desired manner or are sparingly soluble and hence have no advantages over the water-insoluble phosphates described above.

It was therefore an object of the present invention to provide water-absorbing polymer particles with high centrifuge retention capacity (CRC) and high gel bed permeability (GBP).

It was a further object of the present invention to provide suitable coatings for water-absorbing polymer particles, which are easy to apply, do not have any dusting or tackiness problems and do not lead to excessive corrosion in the process for producing the water-absorbing polymer particles.

It was a further object of the present invention to provide suitable coatings for water-absorbing polymer particles, which are easy to apply from aqueous solution and do not have any use problems owing to sparingly soluble or insoluble salts of polyvalent cations.

The object is achieved by providing water-absorbing polymer particles comprising
a) at least one polymerized ethylenically unsaturated monomer which bears acid groups and may be at least partly neutralized,
b) at least one polymerized crosslinker,
c) optionally one or more ethylenically unsaturated monomers copolymerized with the monomers mentioned under a),
d) optionally one or more water-soluble polymers and
e) at least one reacted surface postcrosslinker,
said water-absorbing polymer particles having been coated with at least one complex consisting of a polyvalent metal salt of the general formula (I)

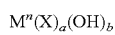
$$M^n(X)_a(OH)_b \quad (I)$$

and a 2-hydroxycarboxamide, in which
M is at least one polyvalent metal cation,
X is at least one acid anion,
a is a number from 0 to n/m, where m is the number of negative charges of the acid anion and n is the number of positive charges of the polyvalent metal cation, and
b is a number from 0 to n.

Suitable acid anions X are, for example, anions of acids selected from the group of glyceric acid, citric acid, glycolic acid, lactic acid, lactoyllactic acid, malonic acid, hydroxymalonic acid, tartaric acid, glycerol-1,3-diphosphoric acid, glycerolmonophosphoric acid, acetic acid, formic acid, propionic acid, methanesulfonic acid and sulfuric acid. Preference is given to anions of acetic acid, propionic acid, glycolic acid, lactic acid, methanesulfonic acid and sulfuric acid.

The polyvalent metal salts of the general formula (I) may also be pure hydroxides of polyvalent metal cations.

Suitable polyvalent metal cations are the cations of aluminum, zirconium, iron, titanium, zinc, calcium, magnesium and strontium. Preferred cations are those of aluminum, zirconium, titanium and iron; more preferred cations are those of aluminum, titanium and zirconium; the most preferred cation is that of aluminum.

In one embodiment particularly preferred in accordance with the invention, pure aluminum hydroxide was used.

Suitable 2-hydroxycarboxamides are the amides of malic acid, glycolic acid, isocitric acid, mandelic acid, lactic acid, tartronic acid, tartaric acid and citric acid. Preference is given to glycolamide and lactamide; most preferred is lactamide.

The complex of a polyvalent metal salt of the general formula (I) and a 2-hydroxycarboxamide comprises preferably from 0.1 to 3 mol, more preferably from 0.3 to 2 mol and most preferably from 0.5 to 1.5 mol of the 2-hydroxycarboxamide, based in each case on the polyvalent metal cation.

The inventive water-absorbing polymer particles comprise preferably 0.001 to 5% by weight, more preferably 0.01 to 2% by weight and most preferably 0.1 to 1% by weight of the complex of a polyvalent metal salt and a 2-hydroxycarboxamide.

The degree of neutralization of the polymerized monomer a) may vary from 0 to 100 mol %, and is typically in the range of 30 to 90 mol %. In order to achieve the object of the invention, it may, however, be necessary to select the degree of neutralization such that an optimal absorption capacity is combined with good liquid conductivity. Therefore, the acid groups of the polymerized monomer a) have preferably been neutralized to an extent of greater than 45 mol %, more preferably to an extent of greater than 55 mol %, especially preferably to an extent of greater than 65 mol %, very especially preferably to an extent of greater than 68 mol %, and preferably to an extent of at most 80 mol %, more preferably to an extent of at most 76 mol %, especially preferably to an extent of at most 74 mol %, very especially preferably to an extent of at most 72 mol %.

Suitable monomers for the polymerized monomer a), the polymerized crosslinker b) and the polymerized monomer c) are the monomers i), crosslinkers ii) and monomers iii) described below.

Suitable water-soluble polymers for the water-soluble polymers d) are the water-soluble polymers iv) described below.

Suitable surface postcrosslinkers for the reacted surface postcrosslinkers e) are the surface postcrosslinkers v) described below.

The water-absorbing polymer particles typically have a particle size up to at most 1000 μm, the particle size preferably being below 900 μm, preferentially below 850 μm, more preferably below 800 μm, even more preferably below 700 μm, most preferably below 600 μm. The water-absorbing polymer particles have a particle size of at least 50 μm, preferably at least 100 μm, more preferably of at least 150 μm, even more preferably of at least 200 μm, most preferably of at least 300 μm. The particle size can be determined by EDANA recommended test method No. WSP 220.2-05 "Particle Size Distribution".

Preferably less than 2% by weight, more preferably less than 1.5% by weight and most preferably less than 1% by weight of the water-absorbing polymer particles have a particle size of less than 150 μm.

Preferably less than 2% by weight, more preferably less than 1.5% by weight and most preferably less than 1% by weight of the water-absorbing polymer particles have a particle size of more than 850 μm.

Preferably at least 90% by weight, more preferably at least 95% by weight, especially preferably at least 98% by weight and very especially preferably at least 99% by weight of the water-absorbing polymer particles have a particle size of 150 to 850 μm.

In a preferred embodiment, at least 90% by weight, preferably at least 95% by weight, more preferably at least 98% by weight and most preferably at least 99% by weight of the water-absorbing polymer particles have a particle size of 150 to 700 μm.

In a further preferred embodiment, at least 90% by weight, preferably at least 95% by weight, more preferably at least 98% by weight and most preferably at least 99% by weight of the water-absorbing polymer particles have a particle size of 200 to 700 μm.

In a further, more preferred embodiment, at least 90% by weight, preferably at least 95% by weight, more preferably at least 98% by weight and most preferably at least 99% by weight of the water-absorbing polymer particles have a particle size of 150 to 600 μm.

In a further, even more preferred embodiment, at least 90% by weight, preferably at least 95% by weight, more preferably at least 98% by weight and most preferably at least 99% by weight of the water-absorbing polymer particles have a particle size of 200 to 600 μm.

In a further, especially preferred embodiment, at least 90% by weight, preferably at least 95% by weight, more preferably at least 98% by weight and most preferably at least 99% by weight of the water-absorbing polymer particles have a particle size of 300 to 600 μm.

The water content of the inventive water-absorbing polymer particles is preferably less than 6% by weight, more preferably less than 4% by weight and most preferably less than 3% by weight. Higher water contents are of course also possible, but typically reduce the absorption capacity and are therefore not preferred.

The surface tension of the aqueous extract of the swollen water-absorbing polymer particle at 23° C. is typically at least 0.05 N/m, preferably at least 0.055 N/m, more preferably at least 0.06 N/m, especially preferably at least 0.065 N/m, very especially preferably at least 0.068 N/m.

The centrifuge retention capacity (CRC) of the water-absorbing polymer particles is typically at least 24 g/g, preferably at least 26 g/g, more preferably at least 28 g/g, especially preferably at least 30 g/g, very especially preferably at least 34 g/g, and typically not more than 50 g/g.

The absorbency under a pressure of 49.2 g/cm$^2$ (AUL0.7 psi) of the water-absorbing polymer particles is typically at least 15 g/g, preferably at least 17 g/g, more preferably at least 20 g/g, especially preferably at least 22 g/g, even more preferably at least 24 g/g, and typically not more than 45 g/g.

The gel bed permeability (GBP) of the water-absorbing polymer particles is, for example, at least 10 darcies, typically at least 15 darcies, preferably at least 20 darcies, more preferably at least 25 darcies, especially preferably at least 30 darcies, most preferably at least 35 darcies, and typically not more than 200 darcies.

Preferred inventive water-absorbing polymer particles are polymer particles with the abovementioned properties.

The present invention further provides a process for producing water-absorbing polymer particles by polymerizing a monomer solution or suspension comprising
i) at least one ethylenically unsaturated monomer which bears acid groups and may be at least partly neutralized,
ii) at least one crosslinker,
iii) optionally one or more ethylenically unsaturated monomers copolymerizable with the monomers mentioned under i) and
iv) optionally one or more water-soluble polymers,
and drying, grinding and classifying the resulting polymer gel, coating it with
v) at least one surface postcrosslinker
and thermally surface postcrosslinking it, wherein the water-absorbing polymer particles are coated before, during or after the thermal surface postcrosslinking with at least one complex consisting of a polyvalent metal salt of the general formula (I)

(I)

and a 2-hydroxycarboxamide, in which
M is at least one polyvalent metal cation,
X is at least one acid anion,
a is a number from 0 to n/m, where m is the number of negative charges of the acid anion and n is the number of positive charges of the polyvalent metal cation, and
b is a number from 0 to n.

Suitable acid anions X are, for example, anions of acids selected from the group of glyceric acid, citric acid, glycolic acid, lactic acid, lactoyllactic acid, malonic acid, hydroxymalonic acid, tartaric acid, glycerol-1,3-diphosphoric acid, glycerolmonophosphoric acid, acetic acid, formic acid, propionic acid, methanesulfonic acid and sulfuric acid. Preference is given to anions of acetic acid, propionic acid, glycolic acid, lactic acid, methanesulfonic acid and sulfuric acid.

It is also possible to use pure hydroxides of polyvalent metal cations.

Suitable polyvalent metal cations are the cations of aluminum, zirconium, iron, titanium, zinc, calcium, magnesium and strontium. Preferred cations are those of aluminum, zirconium, titanium and iron; more preferred cations are those of aluminum, titanium and zirconium; the most preferred cation is that of aluminum.

In one embodiment particularly preferred in accordance with the invention, pure aluminum hydroxide is used.

The polyvalent metal salts of the general formula (I) can be prepared by reacting a hydroxide, for example aluminum hydroxide or sodium aluminate, with at least one acid, for example sulfuric acid. The reaction is effected preferably in aqueous solution or dispersion.

Suitable 2-hydroxycarboxamides are the amides of malic acid, glycolic acid, isocitric acid, mandelic acid, lactic acid, tartronic acid, tartaric acid and citric acid. Preference is given to glycolamide and lactamide; most preferred is lactamide.

The complexes of a polyvalent metal salt of the general formula (I) and a 2-hydroxycarboxamide can be prepared by reacting a polyvalent metal salt of the general formula (I) with a 2-hydroxycarboxamide.

The complex of a polyvalent metal salt of the general formula (I) and a 2-hydroxycarboxamide comprises preferably from 0.1 to 3 mol, more preferably from 0.3 to 2 mol and most preferably from 0.5 to 1.5 mol of the 2-hydroxycarboxamide, based in each case on the polyvalent metal cation.

Coating is accomplished using preferably 0.001 to 5% by weight, more preferably 0.01 to 2% by weight and most preferably 0.1 to 1% by weight of the complex of a polyvalent metal salt and a 2-hydroxycarboxamide.

In a further embodiment, at least one surface postcrosslinker added to the aqueous solution or dispersion of the at least one complex of a polyvalent metal salt of the general formula (I) and a 2-hydroxycarboxamide before, during or after the synthesis thereof is preferably from the group of ethylene glycol, propylene glycol, 1,3-propanediol, 1,4-butanediol, glycerol, N-(2-hydroxyethyl)-2-oxazolidone, 2-oxazolidone, ethylene carbonate and propylene carbonate. With regard to the amounts for the added amounts, the restrictions regarding surface postcrosslinking as specified below apply.

The solution thus prepared is used directly or in further-diluted form. A particular advantage of this embodiment is an increased storage stability of the solutions thus prepared.

The aqueous solution of the at least one complex of a polyvalent metal salt of the general formula (I) and a 2-hydroxycarboxamide is generally a true solution or a colloidal solution, but sometimes also a suspension.

The water-absorbing polymer particles are typically water-insoluble.

The monomers i) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers i) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers i) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers i). Suitable purification processes are described, for example, in WO 2002/055469 A1, WO 2003/078378 A1 and WO 2004/035514 A1. A suitable monomer a) is, for example, acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers i) is preferably at least 50 mol %, more preferably at least 90 mol %, most preferably at least 95 mol %.

The monomers i) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers ii) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers ii).

Crosslinkers ii) are preferably compounds having at least two polymerizable groups which can be polymerized free-radically into the polymer network. Suitable crosslinkers ii) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers ii) are especially N,N'-methylenebisacrylamide and N,N'-methylenebismethacrylamide, esters of unsaturated mono- or polycarboxylic acids of polyols, such as diacrylates or triacrylates, for example butanediol diacrylate, ethylene glycol diacrylate and trimethylolpropane triacrylate, and allyl compounds, such as allyl acrylate, allyl methacrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described, for example, in EP 0 343 427 A1. Other suitable crosslinkers ii) are pentaerythritol diallyl ether, pentaerythritol triallyl ether and pentaerythritol tetraallyl ether, polyethylene glycol diallyl ether, ethylene glycol diallyl ether, glycerol diallyl ether and glycerol triallyl ether, sorbitol-based polyallyl ethers, and ethoxylated variants of these. In the process according to the invention, it is possible to use diacrylates and dimethacrylates of polyethylene glycols, the polyethyllene glycol used having a molecular weight between 300 and 1000.

However, particularly advantageous crosslinkers ii) are di- and triacrylates of 3- to 15-tuply ethoxylated glycerol, of 3- to 15-tuply ethoxylated trimethylolpropane, especially di- and triacrylates of 3-tuply ethoxylated glycerol or of trimethylolpropane, of 3-tuply propoxylated glycerol or trimethylolpropane, and also of 3-tuply mixed ethoxylated or propoxylated glycerol or trimethyllolpropane, of 15- to 25-tuply ethoxylated glycerol, trimethylolethane or trimethylolpropane, and also of 40-tuply ethoxylated glycerol, trimethylolethane or trimethylolpropane.

Very particularly preferred crosslinkers ii) are the polyethoxylated and/or -propoxylated glycerols which have been esterified with acrylic acid or methacrylic acid to di- or triacrylates or di- or tri-methacrylates, as described, for example, in DE 103 19 462 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol. These are notable for particularly low residual contents (typically below 10 ppm) in the water-absorbing polymer particles and the aqueous extracts of the swollen water-absorbing polymer particles produced therewith have an almost unchanged surface tension (typically at least 0.068 N/m at 23° C.) compared to water at the same temperature.

The amount of crosslinker ii) is preferably 0.05 to 2.5% by weight, more preferably 0.1 to 1% by weight and most preferably 0.3 to 0.6% by weight, based in each case on monomer i). With rising crosslinker content, the centrifuge retention capacity (CRC) falls and the absorbency under a pressure of 21.0 g/cm$^2$ (AUL0.3 psi) passes through a maximum.

Examples of ethylenically unsaturated monomers iii) which are copolymerizable with the monomers i) are acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

The water-soluble polymers iv) used may be polyvinyl alcohol, polyvinylamine, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer i), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution or suspension can therefore be freed of dissolved oxygen before the polymerization by inertization, i.e. flowing an inert gas through, preferably nitrogen or carbon dioxide. The oxygen content of the monomer solution or suspension is preferably lowered before the polymerization to less than 1 ppm by weight, more preferably to less than 0.5 ppm by weight, most preferably to less than 0.1 ppm by weight.

For better control of the polymerization reaction, it is optionally possible to add all known chelating agents to the monomer solution or suspension or to the raw materials thereof. Suitable chelating agents are, for example, phosphoric acid, diphosphoric acid, triphosphoric acid, polyphosphoric acid, citric acid, tartaric acid, and salts thereof.

Further suitable examples are iminodiacetic acid, hydroxyethyliminodiacetic acid, nitrilotriacetic acid, nitrilotripropionic acid, ethylenediaminetetraacetic acid, diethylenetriaminepentaacetic acid, triethylenetetraaminehexaacetic acid, N,N-bis(2-hydroxyethyl)glycine and trans-1,2-diaminocyclohexanetetraacetic acid, and salts thereof. The amount used is typically 1 to 30 000 ppm based on the monomers i), preferably 10 to 1000 ppm, preferentially 20 to 600 ppm, more preferably 50 to 400 ppm, most preferably 100 to 300 ppm.

The preparation of a suitable base polymer and further suitable monomers i) are described, for example, in DE 199 41 423 A1, EP 0 686 650 A1, WO 2001/45758 A1 and WO 2003/104300 A1.

The reaction is preferably performed in a kneader, as described in WO 2001/038402 A1, or on a belt reactor, as described in EP 0 955 086 A1. Also advantageous, however, is production by the process of inverse suspension polymerization or of droplet polymerization. In both processes, rounded base polymer particles are obtained, often even with spherical morphology.

The morphology of the base polymer particles can be selected as desired; for example, it is possible to use irregular particles in the form of fragments with smooth surfaces, irregular particles with rough surfaces, particle aggregates, rounded particles or spherical particles.

The polymerization is advantageously brought about by thermal and/or redox initiator systems. Suitable thermal initiators are azo initiators, peroxodisulfates, peroxodiphosphates and hydroperoxides. Peroxo compounds such as hydrogen peroxide, tert-butyl hydroperoxide, ammonium persulfate, potassium persulfate and sodium persulfate are preferably also used as at least one initiator component in redox initiator systems. Peroxide can, for example, also be obtained in situ by reduction of the oxygen present by means of a mixture of glucose and glucose oxidase or by means of other enzymatic systems.

The reduction components used may, for example, be ascorbic acid, bisulfite, thiosulfate, 2-hydroxy-2-sulfonatoacetic acid, 2-hydroxy-2-sulfinatoacetic acid, or salts thereof, polyamines, for example N,N,N',N'-tetramethylethylenediamine.

The acid groups of the resulting polymer gels have preferably been neutralized to an extent of greater than 45 mol %, more preferably to an extent of greater than 55 mol %, especially preferably to an extent of greater than 65 mol %, very especially preferably to an extent of greater than 68 mol %, and preferably to an extent of at most 80 mol %, more preferably to an extent of at most 76 mol %, especially preferably to an extent of at most 74 mol %, very especially preferably to an extent of at most 72 mol %, for which the customary neutralizing agents can be used, for example ammonia, amines, such as ethanolamine, diethanolamine, triethanolamine or dimethylaminoethanolamine, preferably alkali metal hydroxides, alkali metal oxides, alkali metal carbonates or alkali metal hydrogencarbonates and mixtures thereof, particular preference being given to sodium and potassium as alkali metals, but very particular preference being given to sodium hydroxide, sodium carbonate or sodium hydrogencarbonate, and mixtures thereof. It is optionally also possible to use water-soluble alkali metal silicates at least for partial neutralization and to increase the gel strength. Usually, neutralization is obtained by mixing in the neutralizing agent in the form of an aqueous solution or, preferably, also as a solid.

The neutralization can be carried out after the polymerization at the polymer gel stage. However, it is also possible to neutralize up to 40 mol %, preferably 10 to 30 mol %, more preferably 15 to 25 mol %, of the acid groups before the polymerization, by adding a portion of the neutralizing agent directly to the monomer solution, and only establishing the desired final degree of neutralization after the polymerization, at the polymer gel stage. The monomer solution can be neutralized by mixing in the neutralizing agent, either to a predetermined preliminary degree of neutralization with subsequent post-neutralization to the final value after or during the polymerization reaction, or the monomer solution is set directly to the final value by mixing in the neutralizing agent before the polymerization. The polymer gel can be mechanically comminuted, for example by means of an extruder, in which case the neutralizing agent can be sprayed on, scattered over or poured on and then cautiously mixed in. To this end, the gel mass obtained can be repeatedly extruded for homogenization.

In the case of an excessively low degree of neutralization, in the course of the subsequent drying and during the subsequent surface postcrosslinking of the base polymer, there are unwanted thermal crosslinking effects which can greatly reduce the centrifuge retention capacity (CRC) of the water-absorbing polymer particles, up to the extent that they are unusable.

In the case of an excessively high degree of neutralization, however, there is less efficient surface postcrosslinking, which leads to a reduced saline flow conductivity (SFC) of the water-absorbing polymer particles.

An optimal result is obtained, in contrast, when the degree of neutralization of the base polymer is adjusted such that efficient surface postcrosslinking is achieved, and hence a high saline flow conductivity (SFC), while at the same time neutralizing to such an extent that the polymer gel can be dried in the course of production in a standard belt dryer or other drying apparatus customary on the industrial scale, without loss of centrifuge retention capacity (CRC).

Before the drying, the polymer gel can still be mechanically processed further in order to comminute remaining lumps or to homogenize the size and structure of the gel particles. For this purpose, it is possible to use stirring, kneading, shaping, shearing and cutting tools. Excessive shear stress, however, can damage the polymer gel. In general, mild mechanical further processing leads to an improved drying outcome, since the more regular gel particles dry more homogeneously and have a lesser tendency to bubbles and lumps.

The neutralized polymer gel is then dried with a belt dryer, fluidized bed dryer, shaft dryer or roller dryer until the residual moisture content is preferably below 10% by weight, especially below 5% by weight, the residual moisture content being determined by EDANA recommended test method No. WSP 230.2-05 "Moisture content". Thereafter, the dried polymer gel is ground and screened, usable grinding equipment typically including roll mills, pin mills or vibrating mills, and screens with mesh sizes needed to produce the water-absorbing polymer particles being used.

The base polymers are subsequently surface postcrosslinked. Surface postcrosslinkers v) suitable for this purpose are compounds which comprise at least two groups which can form covalent bonds with the carboxylate groups of the polymers. Suitable compounds are, for example, alkoxysilyl compounds, polyaziridines, polyamines, polyamidoamines, di- or polyglycidyl compounds, as described in EP 0 083 022 A2, EP 0 543 303 A1 and EP 0 937 736 A2, polyhydric alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230. Also suitable are compounds with mixed functionality, such as glycidol, 3-ethyl-3-oxetanemethanol (trimethylolpropaneoxetane), as described in EP 1 199 327 A1, aminoethanol, diethanolamine, triethanolamine, or compounds which, after the first reaction, form a further functionality, such as ethylene oxide, propylene oxide, isobutylene oxide, aziridine, azetidine or oxetane.

Additionally described as suitable surface postcrosslinkers v) are cyclic carbonates in DE 40 20 780 C1,2-oxazolidinone and derivatives thereof, such as 2-hydroxyethyl-2-oxazolidinone, in DE 198 07 502 A1, bis- and poly-2-oxazolidinones in DE 198 07 992 C1,2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and derivatives thereof in WO 2003/031482 A1.

The surface postcrosslinking is typically performed by spraying a solution of the surface postcrosslinker onto the aqueous polymer gel or the dry base polymer particles. The spray application is followed by thermal surface postcrosslinking, in which case drying may take place either before or during the surface postcrosslinking reaction.

Preferred surface postcrosslinkers v) are amide acetals or carbamic esters of the general formula (II)

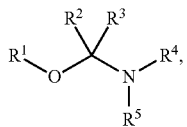

(II)

in which
$R^1$ is $C_1$-$C_{12}$-alkyl, $C_2$-$C_{12}$-hydroxyalkyl, $C_2$-$C_{12}$-alkenyl or $C_6$-$C_{12}$-aryl,
$R^2$ is Z or $OR^6$
$R^3$ is hydrogen, $C_1$-$C_{12}$-alkyl, $C_2$-$C_{12}$-hydroxyalkyl, $C_2$-$C_{12}$-alkenyl or $C_6$-$C_{12}$-aryl, or Z,
$R^4$ is $C_1$-$C_{12}$-alkyl, $C_2$-$C_{12}$-hydroxyalkyl, $C_2$-$C_{12}$-alkenyl or $C_6$-$C_{12}$-aryl,
$R^5$ is hydrogen, $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl, $R^6$ is $C_1$-$C_{12}$-alkyl, $C_2$-$C_{12}$-hydroxyalkyl, $C_2$-$C_{12}$-alkenyl or $C_6$-$C_{12}$-aryl and
Z is a carbonyl oxygen common to the $R^2$ and $R^3$ radicals, where $R^1$ and $R^4$ and/or $R^5$ and $R^6$ may be a bridged C2- to C6-alkanediyl and where the abovementioned $R^1$ to $R^6$ radicals may also have a total of from one to two free valences and may be joined to at least one suitable base structure by these free valences,
or polyhydric alcohols, the polyhydric alcohol preferably having a molecular weight of less than 100 g/mol, preferably of less than 90 g/mol, more preferably of less than 80 g/mol, most preferably of less than 70 g/mol, per hydroxyl group, and no vicinal, geminal, secondary or tertiary hydroxyl groups, and polyhydric alcohols are either diols of the general formula (IIIa)

HO—$R^7$—OH (IIIa)

in which $R^7$ is either an unbranched dialkyl radical of the formula —$(CH_2)_p$— where p is an integer from 2 to 20, preferably from 3 to 12, and both hydroxyl groups are terminal, or $R^7$ is an unbranched, branched or cyclic dialkyl radical, or polyols of the general formula (IIIb)

(IIIb)

in which the $R^8$, $R^9$, $R^{10}$, $R^{11}$ radicals are each independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxyethyl, 2-hydroxyethyl, 3-hydroxypropyl or 4-hydroxybutyl, and a total of 2, 3 or 4, preferably 2 or 3, hydroxyl groups are present, and not more than one of the $R^8$, $R^9$, $R^{19}$ and $R^{11}$ radicals is hydroxyl,
or cyclic carbonates of the general formula (IV)

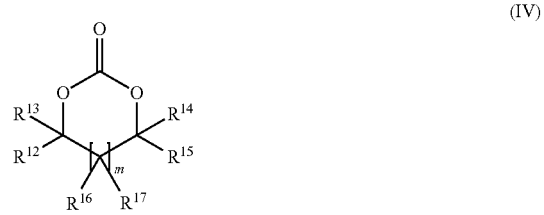

(IV)

in which $R^{12}$, $R^{13}$, $R^{14}$, $R^{15}$, $R^{16}$ and $R^{17}$ are each independently hydrogen, methyl, ethyl, n-propyl, isopropyl, n-butyl, sec-butyl or isobutyl, and m is either 0 or 1,
or bisoxazolines of the general formula (V)

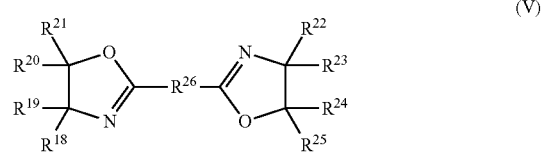

(V)

in which $R^{18}$, $R^{19}$, $R^{20}$, $R^{21}$, $R^{22}$, $R^{23}$, $R^{24}$ and $R^{25}$ are each independently hydrogen, methyl, ethyl, n-propyl, isopropyl, n-butyl, sec-butyl or isobutyl, and $R^{26}$ is a single bond, a linear, branched or cyclic $C_1$-$C_{12}$-dialkyl radical, or a polyalkoxydiyl radical which is formed from one to ten ethylene oxide and/or propylene oxide units, as possessed, for example, by polyglycoldicarboxylic acids.

The preferred surface postcrosslinkers v) are exceptionally selective. Side reactions and further reactions which lead to volatile and hence malodorous compounds are minimized. The water-absorbing polymer particles prepared with the preferred surface postcrosslinkers v) are therefore odor-neutral even in the moistened state.

Owing to their low reactivity, polyhydric alcohols as surface postcrosslinkers v) require high surface postcrosslinking temperatures. Alcohols which have vicinal, geminal, secondary and tertiary hydroxyl groups form by-products which are unwanted in the hygiene sector, which lead to unpleasant odors and/or discoloration of the hygiene article in question during production or use.

Preferred surface postcrosslinkers v) of the general formula (II) are 2-oxazolidones such as 2-oxazolidone and N-hydroxyethyl-2-oxazolidone.

Preferred surface postcrosslinkers v) of the general formula (IIIa) are 1,3-propanediol, 1,4-butanediol, 1,5-pentanediol, 1,6-hexanediol and 1,7-heptanediol. Further examples of surface postcrosslinkers of the formula (IIIa) are 1,3-butanediol, 1,8-octanediol, 1,9-nonanediol and 1,10-decanediol.

The diols of the general formula (IIIa) are preferably water-soluble, these diols being water-soluble at 23° C. to an extent of at least 30% by weight, preferably to an extent of at least 40% by weight, more preferably to an extent of at least 50% by weight and most preferably at least to an extent of 60% by weight, for example 1,3-propanediol and 1,7-heptanediol. Even more preferred are those surface postcrosslinkers which are liquid at 25° C.

Preferred surface postcrosslinkers v) of the general formula (IIIb) are butane-1,2,3-triol, butane-1,2,4-triol, glycerol, trimethylolpropane, trimethylolethane, pentaerythritol, 1- to 3-tuply ethoxylated glycerol, trimethylolethane or trimethylolpropane and 1- to 3-tuply propoxylated glycerol, trimethylolethane or trimethylolpropane. Additionally preferred are 2-tuply ethoxylated or propoxylated neopentyl glycol. Particular preference is given to 2-tuply and 3-tuply ethoxylated glycerol and trimethylolpropane.

Preferred polyhydric alcohols of the general formulae (IIIa) and (IIIb) have, at 23° C., a viscosity of less than 3000 mPas, preferably less than 1500 mPas, more preferably less than 1000 mPas, especially preferably less than 500 mPas and very especially preferably less than 300 mPas.

Particularly preferred surface postcrosslinkers v) of the general formula (IV) are ethylene carbonate and propylene carbonate.

A particularly preferred surface postcrosslinker v) of the general formula (V) is 2,2'-bis(2-oxazoline).

The at least one surface postcrosslinker v) is typically used in an amount of at most 0.3% by weight, preferably of at most 0.15% by weight and more preferably of 0.001 to 0.095% by weight, based in each case on the base polymer, as an aqueous solution.

It is possible to use a single surface postcrosslinker v) from the above selection, or any desired mixtures of different surface postcrosslinkers.

The aqueous surface postcrosslinker solution may, as well as the at least one surface postcrosslinker v), typically also comprise a cosolvent.

Cosolvents of good suitability for technical purposes are $C_1$- to $C_6$-alcohols, such as methanol, ethanol, n-propanol, isopropanol, n-butanol, sec-butanol, tert-butanol or 2-methyl-1-propanol, $C_2$- to $C_5$-diols, such as ethylene glycol, propylene glycol or 1,4-butanediol, ketones such as acetone, or carboxylic esters such as ethyl acetate. A disadvantage of many of these cosolvents is that they have typical intrinsic odors.

The cosolvent itself is ideally not a surface postcrosslinker under the reaction conditions. However, in the limiting case and depending on residence time and temperature, the cosolvent may partly contribute to surface postcrosslinking. This is the case especially when the surface postcrosslinker v) is relatively slow to react and can therefore also constitute its own cosolvent, as is the case, for example, when cyclic carbonates of the general formula (IV), diols of the general formula (IIIa) or polyols of the general formula (IIIb) are used. Such surface postcrosslinkers v) can also be used in the function as a cosolvent in a mixture with more reactive surface postcrosslinkers v), since the actual surface postcrosslinking reaction can then be performed at lower temperatures and/or with shorter residence times than in the absence of the more reactive surface postcrosslinker v). Since the cosolvent is used in relatively large amounts and some also remains in the product, it must not be toxic.

In the process according to the invention, the diols of the general formula (IIIa), the polyols of the general formula (IIIb) and the cyclic carbonates of the general formula (IV) are also suitable as cosolvents. They fulfill this function in the presence of a reactive surface postcrosslinker v) of the general formula (II) and/or (V), and/or of a di- or triglycidyl crosslinker. Preferred cosolvents in the process according to the invention are, however, especially the diols of the general formula (IIIa).

Further cosolvents which are particularly preferred in the process according to the invention are the polyols of the general formula (IIIb). Especially preferred among these are the 2- to 3-tuply alkoxylated polyols. Particularly suitable cosolvents are also 3- to 15-tuply, very particularly 5- to 10-tuply, ethoxylated polyols based on glycerol, trimethylolpropane, trimethylolethane or pentaerythritol. Particularly suitable is 7-tuply ethoxylated trimethylolpropane.

Particularly preferred combinations of low-reactivity surface postcrosslinker v) as a cosolvent and reactive surface postcrosslinker v) are combinations of preferred polyhydric alcohols, diols of the general formula (IIIa) and polyols of the general formula (IIIb), with amide acetals or carbamic esters of the general formula (II).

Very particularly preferred combinations are 2-oxazolidone/1,3-propanediol, 2-oxazolidone/propylene glycol, N-(2-hydroxyethyl)-2-oxazolidone/1,3-propanediol and N-(2-hydroxyethyl)-2-oxazolidone/propylene glycol.

Further preferred combinations are propylene glycol/1,4-butanediol, propylene glycol/1,3-propanediol, 1,3-propanediol/1,4-butanediol, dissolved in water and/or isopropanol as a non-reactive solvent.

Further preferred surface postcrosslinker mixtures are ethylene carbonate/water and 1,3-propanediol/water. These can optionally be used in a mixture with isopropanol.

Frequently, the concentration of the cosolvent in the aqueous surface postcrosslinker solution is from 15 to 50% by weight, preferably from 15 to 40% by weight, more preferably from 20 to 35% by weight, based on the solution. In the case of cosolvents which have only limited miscibility with water, the aqueous surface postcrosslinker solution will advantageously be adjusted such that only one phase is present, optionally by lowering the concentration of the cosolvent.

In a preferred embodiment, no cosolvent is used. The at least one surface postcrosslinker v) is then employed only as a solution in water, optionally with addition of a deagglomeration assistant.

The concentration of the at least one surface postcrosslinker v) in the aqueous solution is, for example, 1 to 20% by weight, preferably 1.5 to 10% by weight, more preferably 2 to 5% by weight, based on the solution.

The total amount of the surface postcrosslinker solution based on base polymer is typically from 0.3 to 15% by weight, preferably from 2 to 6% by weight.

In a preferred embodiment, a surfactant as a deagglomeration assistant is added to the base polymer, for example sorbitan monoesters such as sorbitan monococoate and sorbitan monolaurate, or ethoxylated variants thereof. Further very suitable deagglomeration assistants are the ethoxylated and alkoxylated derivatives of 2-propylheptanol, which are sold under the Lutensol XL® and Lutensol XP® brand names (BASF SE, Ludwigshafen, Germany). The deagglomeration assistant can be metered in separately or added to the surface postcrosslinker solution. The deagglomeration assistant is preferably added to the surface postcrosslinker solution.

The amount of the deagglomeration assistant used, based on base polymer, is, for example, up to 0.01% by weight, preferably up to 0.005% by weight and more preferably up to 0.002% by weight. The deagglomeration assistant is preferably metered in such that the surface tension of an aqueous extract of the swollen base polymer and/or of the swollen surface postcrosslinked water-absorbing polymer particles at 23° C. is typically at least 0.05 N/m, preferably at least 0.055 N/m, more preferably at least 0.06 N/m, especially preferably at least 0.065 N/m and very especially preferably 0.068 N/m.

The at least one complex of a polyvalent metal salt of the general formula (I) and a 2-hydroxycarboxamide can be sprayed on as an aqueous solution before, during, together with or after the application of the surface postcrosslinker solution. It can also be applied after completion of the thermal surface postcrosslinking.

Preference is given, however, to application during the application of the surface postcrosslinker solution from at least two parallel nozzles. Most preferred is application together with the surface postcrosslinker solution from a combined solution of the surface postcrosslinker and of the at least one complex of a polyvalent metal salt of the general formula (I) and a 2-hydroxycarboxamide. For this purpose, it is possible to use one or more nozzles to spray on the solution.

The base polymer used in the process according to the invention typically has a residual moisture content after the drying and before application of the surface postcrosslinker solution of less than 10% by weight and preferably less than 5% by weight. Optionally, this moisture content can also be increased to up to 75% by weight, for example by applying water in an upstream spray mixer. The moisture content is determined by EDANA recommended test method No. WSP 230.2-05 "Moisture content". Such an increase in the moisture content leads to slight preliminary swelling of the base polymer and improves the distribution of the surface postcrosslinker on the surface, and the penetration of the particles.

The spray nozzles usable in the process according to the invention are not subject to any restriction. Such nozzles can be supplied with the liquid to be sprayed under pressure. The atomization of the liquid to be sprayed can be effected by expanding it in the nozzle bore on attainment of a particular minimum velocity. In addition, it is also possible to use one-substance nozzles for the inventive purpose, for example slit nozzles or swirl chambers (full-cone nozzles) (for example from Düsen-Schlick GmbH, Germany, or from Spraying Systems Deutschland GmbH, Germany). Such nozzles are also described in EP 0 534 228 A1 and EP 1 191 051 A1.

The spraying is followed by thermal surface postcrosslinking, in which case drying can take place before, during or after the surface postcrosslinking reaction.

The spray application of the surface postcrosslinker solution is preferably performed in mixers with moving mixing tools, such as screw mixers, paddle mixers, disk mixers, plowshare mixers and shovel mixers. Particular preference is given to vertical mixers, very particular preference to plowshare mixers and shovel mixers. Suitable mixers are, for example, Lödige® mixers, Bepex® mixers, Nauta® mixers, Processall® mixers and Schugi® mixers.

The thermal surface postcrosslinking is preferably performed in contact driers, more preferably shovel driers, most preferably disk driers. Examples of suitable driers are Bepex® driers and Nara® driers. Moreover, fluidized bed driers may also be used.

The thermal surface postcrosslinking can be effected in the mixer itself, by heating the jacket or blowing in warm air. Equally suitable is a downstream drier, for example a shelf drier, a rotary tube oven or a heatable screw.

Particular preference is given to applying the surface postcrosslinker solution to the base polymer in a high-speed mixer, for example of the Schugi-Flexomix® or Turbolizer® type, and to thermally surface postcrosslinking it in a reaction dryer, for example of the Nara-Paddle-Dryer® type, or a disk dryer. The base polymer used may still have a temperature of 10 to 120° C. from preceding process steps; the surface postcrosslinker solution may have a temperature of 0 to 150° C. More particularly, the surface postcrosslinker solution can be heated to reduce the viscosity. For the surface postcrosslinking and drying, preference is given to the temperature range from 30 to 220° C., especially 140 to 210° C. and more preferably 160 to 190° C. The preferred residence time at this temperature in the reaction mixer or dryer is below 120 minutes, more preferably below 80 minutes, especially preferably below 50 minutes and most preferably below 30 minutes.

The surface postcrosslinking dryer is purged with air or an inert gas during the drying and surface postcrosslinking reaction, in order to remove the vapors. To promote drying, the dryer and the attached equipment are very substantially heated.

It will be appreciated that cosolvents removed with the vapors can be condensed again outside the reaction dryer and optionally separated by distillation and recycled.

In a preferred embodiment, the surface postcrosslinking reaction and the drying are performed in the absence of oxidizing gases, especially oxygen, the proportion of oxidizing gas in the atmosphere which blankets the water-absorbing polymer particles being less than 10% by volume, preferably less than 1% by volume, more preferably less than 0.1% by volume, especially preferably less than 0.01% by volume and very especially preferably less than 0.001% by volume.

On completion of the reaction drying, the dried water-absorbing polymer particles are cooled. For this purpose, the hot and dry polymer particles are preferably transferred in continuous operation into a downstream cooler. This may, for example, be a disk cooler, a shovel cooler, a fluidized bed cooler or a screw cooler. Cooling is effected via the walls and optionally the stirrer units of the cooler, through which a suitable cooling medium, for example hot or cold water, flows. In the cooler, it is appropriately possible to spray on water or aqueous solutions of additives; this increases the efficiency of the cooling (partial water evaporation). The increased residual moisture content reduces the dust content of the product.

Suitable additives are, for example, fumed silicas and surfactants, which prevent the caking of the polymer particles on addition of water. Optionally, it is also possible here to apply an aqueous solution of the at least one complex of a polyvalent metal salt of the general formula (I) and a 2-hydroxycarboxamide.

Further particularly suitable additives are color-stabilizing additives, for example sodium bisulfite, sodium hypophosphite, phosphate salts, 2-hydroxy-2-sulfonatoacetic acid or salts thereof, 2-hydroxy-2-sulfinatoacetic acid or salts thereof, 1-hydroxyethylidene-1,1-diphosphonic acid or salts thereof, glyoxylic acid or salts thereof, especially the calcium and strontium salts.

Optionally, however, it is also possible merely to cool in the cooler, and to carry out the addition of water and additives in a downstream separate mixer. The cooling stops the reaction by virtue of the temperature going below the reaction temperature, and the temperature need be lowered overall only to such an extent that the product can be packaged without any problem into plastic sacks or into silo trucks.

The water-absorbing polymer particles can optionally be additionally coated with water-insoluble metal phosphates, as described in WO 2002/060983 A1.

Optionally, it is possible to additionally apply all known coatings, such as film-forming polymers, dendrimers, polycationic polymers (such as polyvinylamine, polyethyleneimine or polyallylamine), water-insoluble polyvalent metal salts, such as calcium sulfate, or hydrophilic inorganic particles, such as clay minerals, fumed silica, aluminum oxide and magnesium oxide. This can achieve additional effects, for example a reduced caking tendency, improved processing properties or a further enhancement in saline flow conductivity (SFC). When the additives are used and sprayed on in the form of dispersions, they are preferably used as aqueous dispersions, and preference is given to additionally applying an antidusting agent to fix the additive on the surface of the water-absorbing polymer particles.

The present invention further provides hygiene articles comprising inventive water-absorbing polymer particles, preferably ultrathin diapers, comprising an absorbent core consisting of 50 to 100% by weight, preferably 60 to 100% by weight, more preferably 70 to 100% by weight, especially preferably 80 to 100% by weight and very especially preferably 90 to 100% by weight of inventive water-absorbing polymer particles, of course not including the envelope of the absorbent core.

Very particularly advantageously, the inventive water-absorbing polymer particles are also suitable for production of laminates and composite structures, as described, for example, in US 2003/0181115 and US 2004/0019342. In addition to the hotmelt adhesives described in both documents for production of such novel absorbent structures, and especially the fibers, described in US 2003/0181115, composed of hotmelt adhesives to which the water-absorbing polymer particles are bound, the inventive water-absorbing polymer particles are also suitable for production of entirely analogous structures using UV-crosslinkable hotmelt adhesives, which are sold, for example, as AC-Resin® (BASF SE, Ludwigshafen, Germany). These UV-crosslinkable hotmelt adhesives have the advantage of already being processable at 120 to 140° C.; they therefore have better compatibility with many thermoplastic substrates. A further significant advantage is that UV-crosslinkable hotmelt adhesives are very safe in toxicological terms and also do not cause any evaporation in the hygiene articles. A very significant advantage in connection with the inventive water-absorbing polymer particles is the property of the UV-crosslinkable hotmelt adhesives of not tending to yellow during processing and crosslinking. This is especially advantageous when ultrathin or partly transparent hygiene articles are to be produced. The combination of the inventive water-absorbing polymer particles with UV-crosslinkable hotmelt adhesives is therefore particularly advantageous. Suitable UV-crosslinkable hotmelt adhesives are described, for example, in EP 0 377 199 A1, EP 0 445 641 A1, U.S. Pat. No. 5,026,806, EP 0 655 465 A1 and EP 0 377 191 A1.

Cellulose-free hygiene articles are secured to suitable nonwoven backings by fixing water-absorbing polymer particles by means of thermoplastic polymers, especially of hotmelt adhesives, when these thermoplastic polymers are spun to fine fibers. Such products are described in US 2004/0167486, US 2004/0071363, US 2005/0097025, US 2007/0156108, US 2008/0125735, EP 1 917 940 A2, EP 1 913 912 A1, EP 1 913 913 A2, EP 1 913 914 A1, EP 1 911 425 A2, EP 1 911 426 A2, EP 1 447 067 A1, EP 1 813 237 A2, EP 1 813 236 A2, EP 1 808 152 A2 and EP 1 447 066 A1. The production processes are described in WO 2008/155722 A2, WO 2008/155702 A1, WO 2008/155711 A1, WO 2008/155710 A1, WO 2008/155701 A2, WO 2008/155699 A1. Additionally known are extensible cellulose-free hygiene articles, and US 2006/0004336, US 2007/0135785, US 2005/0137085 disclose the production thereof by simultaneous fiber spinning of suitable thermoplastic polymers and incorporation of pulverulent water-absorbing polymer particles.

The water-absorbing polymer particles are tested by the test methods described hereinafter.

Methods:

The measurements should, unless stated otherwise, be conducted at an ambient temperature of 23±2° C. and a relative air humidity of 50±10%. The water-absorbing polymer particles are mixed thoroughly before the measurement.

Centrifuge Retention Capacity

The centrifuge retention capacity (CRC) is determined by EDANA recommended test method No. WSP 241.2-05 "Centrifuge Retention Capacity", except that the actual sample with the particle size distribution specified therefor is analyzed for each example.

Absorbency Under a Pressure of 49.2 g/cm$^2$

The absorbency under a pressure of 49.2 g/cm$^2$ (AUL0.7 psi) is determined analogously to EDANA recommended test method No. WSP 242.2-05 "Absorption under Pressure", except that a pressure of 49.2 g/cm$^2$ (AUL0.7 psi) is established instead of a pressure of 21.0 g/cm$^2$ (AUL0.3 psi) and the actual sample with the particle size distribution specified therefor is analyzed for each example.

Gel Bed Permeability

The gel bed permeability (GBP) of a swollen gel layer under a pressure of 0.3 psi (2070 Pa) is, as described in US 2005/0256757 (paragraphs [0061] and [0075]), determined as the gel bed permeability of a swollen gel layer of water-absorbing polymer particles.

Free Swell Rate

To determine the free swell rate (FSR), 1.00 g (=W1) of the water-absorbing polymer particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker (=W2). The time interval required for the absorption, which has been measured with the stopwatch, is designated as t. The disappearance of the last liquid droplet on the surface is determined as the time t.

The free swell rate (FSR) is calculated therefrom as follows:

$$FSR[g/gs]=W2/(W1 \times t)$$

If the moisture content of the water-absorbing polymer particles, however, is more than 3% by weight, the weight W1 should be corrected to take account of this moisture content.

The EDANA test methods are obtainable, for example, from EDANA, Avenue Eugène Plasky 157, B-1030 Brussels, Belgium.

EXAMPLES

Production of the Base Polymer

Example 1

By continuously mixing deionized water, 50% by weight sodium hydroxide solution and acrylic acid, an acrylic acid/sodium acrylate solution was prepared such that the degree of neutralization corresponded to 71 mol %. The solids content of the monomer solution was 40% by weight.

The polyethylenically unsaturated crosslinker used was 3-tuply ethoxylated glyceryl triacrylate (purity approx. 85% by weight). The amount used was 1.5 kg of crosslinker per t of monomer solution.

To initiate the free-radical polymerization, per t of monomer solution, 1 kg of a 0.25% by weight aqueous hydrogen peroxide solution, 1.5 kg of a 30% by weight aqueous sodium peroxodisulfate solution and 1 kg of a 1% by weight aqueous ascorbic acid solution were used.

The throughput of the monomer solution was 18 t/h. The reaction solution had a feed temperature of 30° C.

The individual components were metered in the following amounts continuously into a List Contikneter continuous kneader reactor with a capacity of 6.3 m³ (LIST AG, Arisdorf, Switzerland):

| | |
|---|---|
| 18 t/h | of monomer solution |
| 27 kg/h | of 3-tuply ethoxylated glyceryl triacrylate |
| 45 kg/h | of hydrogen peroxide solution/sodium peroxodisulfate solution |
| 18 kg/h | of ascorbic acid solution |

Between the addition point for the crosslinker and the addition sites for the initiators, the monomer solution was inertized with nitrogen.

After approx. 50% of the residence time there was an additional metered addition to the reactor of fines (1000 kg/h) which were obtained from the production process by grinding and sieving. The residence time of the reaction mixture in the reactor was 15 minutes.

The resulting polymer gel was applied to a belt drier. On the belt drier, an air/gas mixture flowed continuously around the polymer gel and dried it. The residence time in the belt drier was 37 minutes.

The dried polymer gel was ground and sieved to a particle size fraction of 150 to 850 µm.

The resulting water-absorbing polymer particles (base polymer) had the following particle size distribution:

| | |
|---|---|
| >800 µm | 2.5% by weight |
| 300 to 600 µm | 82.6% by weight |
| 200 to 300 µm | 11.0% by weight |
| 100 to 200 µm | 3.7% by weight |
| <100 µm | 0.2% by weight |

The resulting water-absorbing polymer particles (base polymer) had a centrifuge retention capacity (CRC) of 38.7 g/g, absorbency under a pressure of 49.2 g/cm² (AUL0.7 psi) of 7.3 g/g and a free swell rate (FSR) of 0.27 g/gs.

Preparation of the Complexes

Example 2

A 500 ml four-neck round-bottom flask was initially charged with 43.0 g (552 mmol) of aluminum hydroxide. The flask was immersed into an oil bath preheated to 80° C. 250 ml of water were added and the mixture was stirred gradually and continuously with a stirrer bar using a magnetic stirrer/hotplate. Subsequently, 49.1 g (552 mmol) of lactamide (purity approx. 98% by weight) were added to the mixture. In addition, a thermometer, a bubble counter and a reflux condenser were attached to the flask and the mixture was stirred at 75° C. overnight (15 h). The solution was subsequently cooled and used directly, without further aftertreatment.

Example 3

The procedure was as in example 2, except that 10.6 g (136 mmol) of aluminum hydroxide, 36.3 g (408 mmol) of lactamide and 120 ml of water were used.

Example 4

The procedure was as in example 2, except that 22.1 g (283 mmol) of aluminum hydroxide, 76.5 g (850 mmol) of lactic acid and 250 ml of water were used.

Surface Postcrosslinking of the Base Polymer

Example 5

A Pflugschar® M5RMK shovel drier of capacity 5 l (Gebr. Lödige Maschinenbau GmbH; Paderborn, Germany) was initially charged with 1.2 kg of base polymer from example 1. At an ambient temperature (23° C.), a nitrogen-operated two-substance nozzle was used to spray on, while stirring (200 rpm), within about 80 seconds, a mixture of 0.07% by weight of N-(2-hydroxyethyl)oxazolidinone, 0.07% by weight of 1,3-propanediol, 1.50% by weight of aluminum hydroxide/lactamide complex from example 2 (approx. 25% by weight aqueous solution), 0.30% by weight of propylene glycol, 1.00% by weight of isopropanol and 1.00% by weight of water, based in each case on the base polymer, and the mixture was stirred (60 rpm) for another 5 minutes. Subsequently, the reactor jacket was heated by means of heating fluid while stirring. The heating was controlled by a closed loop such that the product attained the target temperature of 180° C. as rapidly as possible, and was then heated there stably and while stirring. In the course of this, the reactor was blanketed with nitrogen. Samples were then taken regularly at the times reported in the table (after commencement of heating) and the properties were determined. The results are summarized in table 1.

Example 6

The procedure was as in example 5. The base polymer initially charged in the shovel drier was heated to 50° C. before the mixture was sprayed on. The results are summarized in table 1.

Example 7

The procedure was as in example 5. The base polymer initially charged in the shovel drier was heated to 50° C. before the mixture was sprayed on. Instead of the aluminum hydroxyide/lactamide complex from example 2, the aluminum hydroxide/lactamide complex from example 3 (approx. 25% by weight aqueous solution) was used. The results are summarized in table 1.

Example 8

The procedure was as in example 5. The base polymer initially charged in the shovel drier was heated to 50° C. before the mixture was sprayed on. Instead of the aluminum hydroxyide/lactamide complex from example 2, aluminum trilactate from example 4 (approx. 25% by weight aqueous solution) was used. The results are summarized in table 1.

TABLE 1

| | | Surface postcrosslinking | | | | | |
|---|---|---|---|---|---|---|---|
| Ex. | Complex | Temperature [° C.] | Time [min] | CRC [g/g] | AUL0.7 psi [g/g] | GBP [darcies] | FSR [g/gs] |
| 5 | Ex. 2 | 144 | 20 | 37.1 | 7.4 | 0.2 | 0.45 |
| | | 179 | 40 | 36.9 | 8.0 | 0.4 | 0.43 |
| | | 188 | 60 | 36.5 | 21.2 | 9.4 | 0.28 |
| | | 178 | 80 | 30.4 | 22.0 | 29 | 0.23 |
| | | 180 | 100 | 28.0 | 20.3 | 39 | 0.23 |
| | | 183 | 120 | 28.2 | 20.4 | 40 | 0.17 |
| 6 | Ex. 2 | 153 | 20 | 37.7 | 7.3 | 0.2 | 0.43 |
| | | 181 | 40 | 37.6 | 9.0 | 0.7 | 0.39 |
| | | 185 | 60 | 32.0 | 22.2 | 12 | 0.27 |
| | | 183 | 80 | 30.4 | 20.3 | 26 | 0.32 |
| | | 185 | 100 | 29.9 | 19.6 | 30 | 0.26 |
| | | 186 | 120 | 28.6 | 19.6 | 31 | 0.18 |
| 7 | Ex. 3 | 158 | 20 | 38.9 | 7.1 | 0.1 | 0.30 |
| | | 185 | 40 | 38.5 | 9.0 | 0.2 | 0.32 |
| | | 187 | 60 | 31.5 | 23.5 | 6.3 | 0.28 |
| | | 188 | 80 | 30.3 | 21.5 | 10 | 0.24 |
| | | 185 | 100 | 29.0 | 20.5 | 12 | 0.21 |
| | | 186 | 120 | 28.9 | 20.5 | 16 | 0.16 |
| 8*) | Ex. 4 | 158 | 20 | 37.9 | 7.2 | 0.0 | 0.44 |
| | | 185 | 40 | 34.6 | 11.5 | 0.2 | 0.32 |
| | | 188 | 60 | 32.1 | 23.3 | 2.3 | 0.31 |
| | | 187 | 80 | 28.6 | 22.9 | 7.8 | 0.22 |
| | | 188 | 100 | 28.0 | 21.5 | 11 | 0.26 |
| | | 182 | 120 | 24.2 | 20.4 | 15 | 0.19 |

*)comparative example

The results show that, in the case of use of the inventive complexes, a higher gel bed permeability (GBP) is attained with comparable centrifuge retention capacity (CRC).

The invention claimed is:

1. A process for producing water-absorbing polymer particles by polymerizing a monomer solution or suspension comprising
   i) at least one ethylenically unsaturated monomer which bears an acid group and may be at least partly neutralized,
   ii) at least one crosslinker,
   iii) optionally one or more ethylenically unsaturated monomer copolymerizable with the monomer mentioned under i), and
   iv) optionally one or more water-soluble polymer, and
   drying, grinding, and classifying the resulting polymer gel, coating the resulting water-absorbing polymer particles with
   v) at least one surface postcrosslinker
   and thermally surface postcrosslinking, wherein the water-absorbing polymer particles are coated before, during, or after the thermal surface postcrosslinking with at least one complex consisting of a polyvalent metal salt of the general formula (I)

$$M^n(X)_a(OH)_b \qquad (I)$$

and a 2-hydroxycarboxamide, in which
   M is at least one polyvalent metal cation,
   X is at least one acid anion,
   a is a number from 0 to n/m, where m is the number of negative charges of the acid anion and n is the number of positive charges of the polyvalent metal cation, and
   b is a number from 0 to n.

2. The process according to claim 1, wherein the polyvalent metal cation is selected from the group of $Al^{3+}$, $Ti^{4+}$, and $Zr^{4+}$.

3. The process according to claim 1, wherein the acid anion is selected from the group of acetate, propionate, glycolate, lactate, methanesulfonate, and sulfate.

4. The process according to claim 1, wherein the 2-hydroxycarboxamide is selected from the group of glycolamide and lactamide.

5. The process according to claim 1, wherein the complex comprises from 0.5 to 1.5 mol of the 2-hydroxycarboxamide, based on the polyvalent metal cation.

6. The process according to claim 1, wherein from 0.1 to 1% by weight of the complex is used, based on the water-absorbing polymer particles.

7. The process according to claim 1, wherein the complex is used in the form of an aqueous solution.

* * * * *